United States Patent
Greco et al.

[11] 3,973,971
[45] Aug. 10, 1976

[54] METHOD FOR PREPARING AN IMPROVED CREOSOTE WOOD PRESERVATIVE FROM A COAL TAR CREOSOTE

[75] Inventors: Nicholas P. Greco, Pittsburgh; David A. Webb, Valencia, both of Pa.

[73] Assignee: Koppers Company, Inc., Pittsburgh, Pa.

[22] Filed: Feb. 7, 1975

[21] Appl. No.: 547,859

[52] U.S. Cl. ............ 106/15 R; 106/273 R; 106/273 N; 106/284; 260/621 R; 260/627 R; 260/627 H; 208/2
[51] Int. Cl.² ............ C07C 37/36; C09D 15/00
[58] Field of Search ........ 260/621 R, 621 A, 624 A, 260/627 H, 627 R; 208/2; 106/15 R, 273 N, 273 R, 284

[56] References Cited
UNITED STATES PATENTS

| | | | |
|---|---|---|---|
| 2,446,250 | 8/1948 | Schuman | 260/624 A |
| 2,764,618 | 8/1956 | Cue | 260/621 A |

FOREIGN PATENTS OR APPLICATIONS

| | | | |
|---|---|---|---|
| 1,597,867 | 6/1970 | France | 260/624 A |

*Primary Examiner*—James O. Thomas, Jr.
*Assistant Examiner*—W. B. Lone
*Attorney, Agent, or Firm*—Oscar B. Brumback; Herbert J. Zeh, Jr.; Kenneth J. Stachel

[57] ABSTRACT

An improved creosote wood preservative that has a light color and that forms a non-sticky crud deposit is prepared from a coal tar creosote. The coal tar creosote is reacted with one or more of the following groups of neutral compounds: paraformaldehyde, trioxane; or nitrobenzene, nitrotoluene, nitroxylene, tris (hydroxymethyl) nitromethane; or aluminum, zinc or sulfur, to produce a reacted creosote. This reacted creosote is distilled to yield a distillate, which is the improved creosote wood preservative, and a pitch residue.

8 Claims, No Drawings

METHOD FOR PREPARING AN IMPROVED CREOSOTE WOOD PRESERVATIVE FROM A COAL TAR CREOSOTE

BACKGROUND OF THE INVENTION

This invention relates to a method of preparing an improved creosote wood preservative from coal tar creosote. More particularly, this invention relates to a method of preparing an improved creosote wood preservative that has a more stable, and lighter color than coal tar creosote and that does not form a sticky crud deposit like conventional coal tar creosote.

Creosote has been used to preserve wood from decay and biological attack for many years. Creosote has been used to preserve, almost indefinitely, railroad crossties, wood blocks and timbers for buildings, tanks, bridges, telephone and telegraph and utility poles, crossarms, fence posts, and marine and foundation pilings and the like. Creosote consists principally of liquid and solid aromatic hydrocarbons. A more precise definition of creosote is that it consists of the 200°–400°C boiling fraction of coal tar distillate produced by the high temperature carbonization of bituminous coal. The main constituents of creosote have been classified by W. P. K. Findlay in "Preservation of Timber," Adams and Charles Black, London, 1962 as: (1) tar acids such as phenol, cresol, and xylenol, etc., and (2) tar bases such as pyridine, quinoline and acridine, and (3) neutral oils, such as a mixture of naphthalene, anthracene, and other neutral hydrocarbons.

Although creosote is an excellent wood preservative, it has several disadvantages. One disadvantage is that it has a dark color which is imparted to the treated wood. The color may become darker after exposure of the treated wood to air and light. A second disadvantage is that the creosote forms a sticky crud deposit on the treated wood after the treated wood is exposed to sunlight. Crud is a black sticky substance that can be defined chemically as the carbon disulfide insolubles of creosote after the creosote is exposed to ultraviolet radiation. After creosote is applied to a wooden pole, such as a utility pole, the pole is protected from decay and biological attack but the pole may have a blackish color and deposits of a black sticky substance, crud, often appear after exposure to sunlight.

The Cleveland Electric Illuminating Company has set color specifications, C.E.I. color specifications, for treated wood utility poles. These specifications set in the year 1965 and identified as Ser. No. 073 run from a value of 1 for a light colored creosote treated wood to a value of 9 for black colored treated wood pole. The other values between 1 and 9 are 3, 5, and 7 and they indicate an increased darkening color of the creosote treated wood. To meet the requirements of the utility company, the creosote treated wood must have a C.E.I. value of 5 or less. Wood specimens treated with a conventional creosote or a distillate of a conventional creosote have a C.E.I. value of 8.

One method used in the prior art to lighten the color of creosote is discussed in U.S. Pat. No. 3,046,217, W. F. Hefner et al. In this method the conventional creosote is heated to a temperature of about 100° to 150°C. While the creosote is maintained at this temperature, it is aerated for a period of about one hour. The easily oxidized compounds in the creosote are oxidized to stable oxidation products. Then, the air blown creosote is distilled to a temperature of about 395° to 410°C at atmospheric pressure. The purified light colored creosote is the distillate from the distillation step and the oxidized products remain behind in the residue. Next, the distillate is cooled to a temperature of about 40°C to form crystals rich in anthracene, phenanthrene and carbazole. These crystals are removed from the distillate and the completed purified light colored creosote preservative is recovered.

There is a need in the art for a method of producing a light creosote wood preservative that imparts its light color to the treated wood and retains its light color after prolonged exposure to air and light. There is also a need in the art for a method of producing a light colored creosote wood preservative that does not form a sticky crud on the treated wood after the treated wood is exposed to sunlight.

SUMMARY OF THE INVENTION

In accordance with the present invention a method is provided for preparing an improved creosote wood preservative which imparts a stable light color to the treated wood and which does not form a sticky crud deposit on the treated wood after the treated wood is exposed to sunlight. This method comprises reacting a coal tar creosote with one or more of the following groups of neutral compounds: paraformaldehyde; or nitrobenzene, nitrotoluene, nitroxylene, and tris (hydroxymethyl) nitromethane; or aluminum, zinc, and sulfur, to produce a reacted creosote which is then distilled to produce a distillate and a pitch residue. This distillate is the improved creosote wood preservative having a stable light color and which forms a non-sticky type of crud deposit that easily sheds from the treated wood.

The coal tar creosote used in the process of this invention is a 200°–400°C boiling fraction of the distillate of coal tar that is produced by the carbonization of bituminous coal. The process of this invention also encompasses the use of a coal tar creosote that has been subjected to heat or aeration. A conventional coal tar creosote that may be used is one of the following American Wood-Preservers' Association standard creosotes: P1-65, P7-72, or P13-65. These standard creosotes are also cited in the United States Federal Standards TT-C-645B and TT-C-655(1).

The conditions of reaction of the coal tar creosote with the neutral compounds include an elevated temperature which depends upon the specific neutral compound used but generally is in the range of 250°–320°C. When sulfur is used as the neutral compound, the temperature is in the range of 130°–180°C. The residence time is generally in the range of 5 to 120 minutes but this may be varied by adding a greater or lesser quantity of the neutral compound. The amount of neutral compound added to the creosote for the reaction must be enough to oxidize or react with the tar acids and mainly with the phenolic compounds in the creosote. It is believed, but the process of this invention is not limited by this belief, that the tar acids such as phenolic compounds, which have a tendency of darkening on oxidation, may be largely responsible for the discoloration of the creosote when the creosote is exposed to air and light.

The conditions for distilling the reacted creosote are those used for simple, fractional or vacuum distillation. Preferably the conditions are needed for flash distillation in order to reduce the formation of pitch residue. The vapor temperature is in the range of 250° to 325°C at a pressure of 60 mm but any temperature and pressure corresponding to the end temperature in the range from 395°–410°C at atmospheric pressure may be used. Distillation at these conditions produces some pitch residue and a good yield of distillate. This distillate is the improved creosote wood preservative which may be applied directly to the wood. This improved creosote wood preservative generally contains anthracene, phenanthrene, carbazole which form crystals at a temperature below 40°C. These compounds may be removed from the improved creosote wood preservative or treated to remain in the improved creosote wood preservative at temperatures of 40°C and lower. The treatment involves diluting the improved creosote wood preservative with 20 to 25% by weight of correction oil before this preservative is used to impregnate the wood. The correction oil is a low boiling solvent mixture of methylnaphthalenes and a solvent that is compatible with both methylnaphthalene and the improved creosote wood preservative.

The pitch residue from distillation is recovered and, although it contains high boiling non-distillable compounds of creosote along with the added neutral compound, it can be used for its fuel value, for the production of electrode pitch or for a target pitch. Also, by increasing the reaction time of the reaction between creosote and the neutral compound, the amount of pitch residue, which is produced from the distillation, is increased. If the pitch residue contains any salts of the neutral compound, which is added to the coal tar creosote, most of these salts must be washed from the pitch residue before the pitch residue can be used in the production of electrode pitch.

DETAILED DESCRIPTION OF THE INVENTION

The process of this invention is performed either in a batch or in a continuous operation. When the process of this invention is conducted in a continuous operation, it is preferred to adapt the process of this invention to existing creosote producing plants.

Any coal tar creosote may be used in the process of this invention. Examples of conventional coal tar creosotes, which can be used, are the following American Wood-Preservers' Association standard creosotes: P1-65; P13-65 and P7-72. Also a coal tar creosote which has been subjected to heating or aeration may be used as the starting coal tar creosote for the process of this invention. It is preferred to use a coal tar creosote that has been treated to remove the easily removable tar acids. This treatment reduces the amount of neutral compound needed for the reaction with the coal tar creosote. Such a coal tar creosote would contain tar bases, neutral oils and some tar acids consisting mostly of phenolic compounds. Some 60% of the compounds of this conventional creosote are volatile and have been characterized by gas chromatographic analysis. The compounds in weight percent are:

| Naphthalene | 3.0 | Phenanthrene | 11.4 |
|---|---|---|---|
| Methylnaphthalenes | 1.2 | Anthracene | 3.0 |
| Diphenyl | 0.1 | Carbazole | 5.7 |
| Dimethylnaphthalenes | 1.6 | Methylphenanthrenes | 2.3 |
| Acenaphthene | 5.5 | Fluoranthrene | 5.9 |
| Dibenzofuran | 3.0 | Pyrene | 8.1 |
| Fluorene | 6.0 | Benzofluorene | 2.2 |
| Methylfluorenes | 1.4 | | |

In addition, the tar acids of the creosote may consist of the following in weight percent: 2, 3 and 3, 5 xylenol (7.7); 2, 3, 6 trimethylphenol (4.3); 3, 4 xylenol and 2, 4, 6 trimethylphenol (3.7); pentamethylbenzene (1.1); 2, 3, 5 and 2, 4, 5 trimethylphenol (1.0); 2, 6 xylenol (0.4); 2, 4 and 2, 5 xylenol (0.3).

The coal tar creosote is introduced into a reaction vessel. This reaction vessel may be any reaction vessel familiar to those skilled in the art which is fitted with an agitating device and which is constructed to withstand elevated temperatures. The preferred reaction vessel is a stainless steel reaction vessel. The creosote is heated in this vessel to an elevated temperature with agitation while an amount of one or more of the neutral compounds selected from the following groups of compounds: paraformaldehyde, or nitrobenzene, nitrotoluene, nitroxylene, and tris (hydroxymethyl) nitromethane; or aluminum, zinc and sulfur is gradually introduced into the vessel. The neutral compound may be added as a solid or as an aqueous solution which contains the neutral compounds in any concentration that is soluble. The neutral compounds also may be used with any solvent in which the neutral compound is soluble and that is soluble in coal tar creosote.

When the neutral compound is added to the creosote as an aqueous solution, the creosote should be dehydrated prior to the addition. This dehydration would preclude over dilution of the aqueous neutral compound when the moisture content of the coal tar creosote is substantial. The dehydration is accomplished by heating the creosote to a temperature above the boiling point of water before the addition of the aqueous neutral compound. When the creosote is heated in this manner some crude naphthalene and other low boiling compounds in the creosote may be steam distilled. After these compounds are separated from the aqueous phase they may be added to the distillate which is produced from the distillation of the reacted creosote, thereby including these compounds in the total yield of improved creosote wood preservative.

The mixture of heated creosote and neutral compound is agitated and heated to a reaction temperature that is preferably a reflux temperature. This mixture is refluxed for a residence time in the range of 5 to 120 minutes. A residence time of 5 minutes in a continuous operation is preferred since this is the amount of time that creosote is heated at reflux temperatures in existing creosote producing plants. This residence time may be made shorter by adding a larger quantity of neutral compound or made longer by adding a smaller quantity of neutral compound. This refluxing produces a refluxed creosote which contains creosote and high boiling compounds which are derived from a portion of the coal tar creosote. Depending upon the neutral compound used, the refluxed creosote may also contain oxidation products of the coal tar creosote along with some neutral compound or non-volatile salts of the neutral compound.

After refluxing, the refluxed creosote is preferably cooled to a temperature in the range of 120° to 175°C. This cooling occurs since at preferred conditions the temperature of reflux is higher than the temperature of distillation at the same pressures. Then, this cooled refluxed creosote is distilled in the same vessel where refluxing occurs or in a separate vessel to an end vapor temperature of around 300°C at 60 mm pressure. Any temperature and pressure equivalent to a temperature in the range of 395° to 410°C at atmospheric pressure may be used. This distillation produces a distillate which is the improved creosote wood preservative and a pitch residue which contains the non-distillable, high boiling compounds and the non-volatile salts of the coal tar creosote and the neutral compound.

In the preferred embodiment of this invention the neutral compound refluxed with the conventional coal tar creosote is either paraformaldehyde or tris (hydroxymethyl) nitromethane. It is believed, but the process of this invention is not limited by this belief, that the theory of action of the paraformaldehyde or tris (hydroxymethyl) nitromethane is that they react with the tar acids, especially the phenolic compounds present in the coal tar creosote. These phenolic compounds, which have a tendency of darkening on oxidation, are suspected to be largely responsible for the discoloration of the creosote. The refluxing of coal tar creosote with paraformaldehyde or tris (hydroxymethyl) nitromethane produces reaction products which are non-distillable and which remain in the pitch residue when the refluxed creosote is distilled. Between the use of paraformaldehyde or tris (hydroxymethyl) nitromethane as the neutral compound, it is preferred to use paraformaldehyde. The quantity of paraformaldehyde used in refluxing with the coal tar creosote must be at least 5 weight percent at a residence time of 5 minutes. Smaller quantities may be used at longer residence times or larger quantities may be used at shorter residence times. A convenient manner of adding paraformaldehyde to the coal tar creosote, to be refluxed, is to dissolve the paraformaldehyde in some of the coal tar creosote at a temperature of about 170°C and then gradually add this mixture to the remainder of the coal tar creosote at reflux temperatures. This manner circumvents the feeding of solid paraformaldehyde into a coal tar creosote which would be a difficult task in existing creosote producing plants. The preferred quantity of tris (hydroxymethyl) nitromethane refluxed with coal tar creosote is in the range of 1 to 2 weight percent of coal tar creosote.

In an alternative embodiment of this invention nitrobenzene, nitrotoluene or nitroxylene is used as the neutral compound that is refluxed with a coal tar creosote. It is believed, without limiting the process of this invention, that these compounds act as oxidizing agents when refluxed with the coal tar creosote. They oxidize the phenolic compounds which are present in the coal tar creosote and which are believed to be responsible for the darkening of coal tar creosote when it is exposed to air and light. The products of this oxidation are present in the refluxed creosote and since they are non-distillable, they remain behind in the pitch residue when the refluxed creosote is distilled. The tris (hydroxymethyl) nitromethane contains four functional groups which could act as oxidizing agents with the coal tar creosote and also with the active hydrogen compounds in the coal tar creosote such as phenols, imides and amines. Therefore, tris (hydroxymethyl) nitromethane may act as an oxidizing agent or as a reactant like paraformaldehyde as discussed above. Since tris (hydroxymethyl) nitromethane is expensive, it is more desirable to use nitrobenzene as the neutral compound for refluxing with a coal tar creosote. Nitrobenzene apparently acts as an oxidant when refluxed with the coal tar creosote since water is produced and nitrobenzene is consumed during the refluxing. This oxidation reaction is apparently a rapid reaction since residence times from 0 to 30 minutes give practically the same results. The preferred quantity of nitrobenzene used for refluxing is in the range of 1 to 3 weight percent since varying the quantity of nitrobenzene from 1 to 5 weight percent showed only a slight improvement in the C.E.I. color value. If adequate precautions against the toxicity of nitrobenzene make the use of nitrobenzene uneconomical, then nitrotoluene, which is only 1/10 as toxic as nitrobenzene, may be refluxed with the coal tar creosote instead of nitrobenzene.

In another alternative embodiment of this invention zinc or aluminum may be used as the neutral compound that is refluxed with a coal tar creosote. It is believed without limiting the process of this invention, that the theory of their action is that they form salts with the phenolic compounds in the coal tar creosote. In this manner these metals prevent the phenolic compounds from being distilled when the refluxed creosote is distilled because these phenolic salts remain in the pitch residue after distillation. The refluxing of a coal tar creosote with aluminum or zinc requires longer residence times than the other neutral compounds. When small quantities of these metals, i.e., around 2 weight percent, are used, a residence time in the range of 30 to 120 minutes must be used. It is preferred to add these metals to the coal tar creosote as powdered solids. When zinc was added to the coal tar creosote as a zinc salt for example as zinc sulfate, the salt was insoluble in the creosote and the pitch residue after distillation contained insoluble grains of zinc sulfate.

In another alternative embodiment of this invention the non-metal sulfur is used as the neutral compound that is refluxed with the coal tar creosote. It is believed, without any limitation on the process of this invention, that the sulfur reacts with all the compounds in the coal tar creosote to form condensation products. By using a small amount of sulfur, most of the compounds responsible for the darkening of creosote, when it is contacted by air or light, can be removed. This theory is supported by the fact that large quantities of pitch residue are produced by refluxing coal tar creosote with sulfur and that there is an evolution of hydrogen sulfide during refluxing. The condensation products that are produced are non-distillable and remain in the pitch residue when the refluxed creosote is distilled. The refluxing of the coal tar creosote with sulfur can occur at a temperature in the range of 130°–180°C whereas the other neutral compounds generally reflux with a coal tar creosote at a temperature in the range of 250°–320°C but the temperature depends upon the specific neutral compound used. The lower reflux temperature occurs because hydrogen sulfide gas is evolved during refluxing and this has a cooling effect on the refluxing. The sulfur is preferably added to the coal tar creosote as elemental sulfur in either a liquid or a solid state. The preferred quantity of elemental sulfur refluxed with the coal tar creosote is in the range of 2 to 6 weight percent of the coal tar creosote at a residence time in the range of 2 to 8 minutes. The C.E.I. color value of the distillate produced from the distillation of a refluxed creosote obtained from sulfur refluxing is good, but the evolution of hydrogen sulfide during refluxing and distillation must be controlled. This control may be by any method for collecting hydrogen sulfide known to those skilled in the art.

The distillate from the distillation of the refluxed creosote contains all the neutral oils of the coal tar creosote which give the creosote its preservative value and it may be used directly as the improved creosote wood preservative. Also, the naphthalene and the other low boiling compounds of the coal tar creosote that are recovered by the previous steam distillation may be added to the distillate and this distillate product used as the improved creosote wood preservative. In order to assure that none of the compounds in the improved creosote wood preservative crystallize at low temperature around 40°C a correction oil in the preferred amount of 20 to 25% by weight may be added to the improved creosote wood preservative. The correction oil is a low boiling solvent mixture of methylnaphthalenes and a solvent that is compatible with both the methylnaphthalenes and the improved creosote wood preservative. This addition of correction oil keeps such compounds of the improved creosote wood preservative as anthracene, phenanthrene and carbazole in solution at the low temperatures. Another manner of preventing these compounds from forming crystals in the improved creosote wood preservative is to remove them. This is accomplished by cooling the improved creosote wood preservative below 40°C, crystallizing these compounds and separating them from the improved creosote wood preservative.

The improved creosote wood preservative was tested in laboratory stability and accelerated aging tests. The stability test includes impregnating a wood test block with the improved creosote wood preservative and then exposing the test block to conditions that simulate plant storage. Conditions used to simulate plant storage are a temperature of 70°C at a residence time of 16 hours followed by 8 hours at 25°C with exposure to air. This procedure is repeated three times for a total of 72 hours. The resulting color of the block is measured by visual comparison with a Ser. No. 073, 1965, Cleveland Electric Illuminating Company (C.E.I.) color specification chart. In the accelerated aging tests a southern, yellow pine sapwood containing both spring and summer growth, cut into blocks having dimensions of 2 × 2 × 1/2 inches, is soaked with improved creosote wood preservative containing a correction oil at 80°C for 20 minutes until about 2 grams of the improved creosote wood preservative is absorbed. Then the block is irradiated with ultraviolet radiation in air with a 325 watt Hanovia high pressure mercury ultraviolet lamp for 72 hours at 80°F or 27°C to simulate outdoor exposure conditions. After exposure, the color of the block is measured by visual comparison with the Ser. No. 073, 1965, C.E.I. color chart. Such tests proved that the wood block impregnated with the improved creosote wood preservative had a C.E.I. color value of less than 5 after storage and exposure to outdoor conditions.

The pitch residue from the distillation of the refluxed creosote contains high boiling non-distillable compounds and when aluminum or zinc is used, the pitch residue will also contain phenolic salts. The pitch residue containing aluminum phenolic salts can be used to produce electrode pitch whereas the pitch residue containing zinc phenolic salts can be used only for its fuel value. The pitch residue obtained when paraformaldehyde is used as the neutral compound is hard and brittle and it is ideal for use as a target pitch. The pitch residue from the other neutral compounds can be used both for producing various pitch products and for its fuel value. The amount of pitch residue produced from the distillation increases when the residence time of refluxing is increased regardless of which neutral compound is used. Some of the neutral compounds tend to increase the amount of pitch residue produced from distillation while others tend to decrease the amount produced. Tris (hydroxymethyl) nitromethane increases the amount of pitch residue to 23% by weight of coal tar creosote while nitrotoluene with the same residence time produces a pitch residue of 18% by weight of coal tar creosote (See Table I, runs 16 and 17).

TABLE I

Table I presents data on the treatment of a coal tar creosote with neutral compounds to produce an improved creosote wood preservative having a light color. The data includes the neutral compound used, the residence time of refluxing, the C.E.I. color number before a stability test and after a stability test and the weight percent of recovered distillate.

The coal tar creosote, which was used as a starting material, had the following characteristics:

| | |
|---|---|
| Moisture content | 0.2% by volume |
| Specific gravity at 38°C | 1.106 |
| Composition in percent by weight on a water-free basis boiling at the following temperatures: | |
| Up to 210°C | 0.0 |
| Up to 235°C | 0.0 |
| Up to 270°C | 5.4 |
| Up to 315°C | 28.0 |
| Up to 355°C | 62.8 |
| Residue content of | 37.0 wt. %. |

This coal tar creosote is hereinafter referred to as Creosote A.

In Table I run No. 7 shows that a longer residence time is required to obtain the desired C.E.I. color value when 1% aluminum powder is used as the neutral compound. Run No. 14 shows that either a longer residence time or an increase in the quantity of neutral compound is required when trioxane is used as the neutral compound. Run No. 1 indicates the C.E.I. value obtained when no neutral compound is used. All the other runs indicate a quantity of neutral compound and a residence time that will yield a C.E.I. color value of 5 or less.

Table I

The Treatment of Creosote A
With Neutral Compounds for Color Improvement

| Run No. | Compound Used[1] | Residence Time of Reflux[2] (min.) | CEI No.[3,4] Before[6] Stability Test | After[7] Stability Test | Wt.%[5] Recovered by Distillation | Remarks |
|---|---|---|---|---|---|---|
| 1 | none | 8)[9] | 8 | — | 91 | Creosote distilled only; no treatment. Zinc sulfate not soluble in creosote. Zinc sulfate in residue as |

Table I-continued
The Treatment of Creosote A With Neutral Compounds for Color Improvement

| Run No. | Compound Used[1] | Residence Time of Reflux[2] (min.) | CEI No.[3,4] Before[6] Stability Test | After[7] Stability Test | Wt.%[5] Recovered by Distillation | Remarks |
|---|---|---|---|---|---|---|
| 2 | 4% zinc sulfate | 10 | 5 | — | 84 | insol. grains. Filtered before distilling. 0.8% zinc in creosote 2.1% zinc in residue. |
| 3 | zinc powder in excess | 60 | 5 | — | 77 | Gave a brittle pitch. |
| 4 | 10% paraformaldehyde | 40 | 3 | — | 70 | |
| 5 | 0.6% zinc dust | 60 | 3 | — | 84 | — |
| 6 | 6% sulfur | 2 | 3.5 | — | 66 | $H_2S$ evolution. |
| 7 | 1% aluminum powder | 10 | 6 | — | 80 | — |
| 8 | 2% sulfur | 5 | 3.5 | — | 75 | $H_2S$ evolution. |
| 9 | 4% sulfur | 5 | 4 | — | 76 | $H_2S$ evolution. |
| 10 | 3% tris (hydroxy methyl) nitromethane | 2 | 4 | — | 77 | — |
| 11 | 3% sulfur | 8 | 3.5 | — | 76 | $H_2S$ evolution. |
| 12 | 4% sulfur | 8 | 3.5 | — | 75 | $H_2S$ evolution. Air at 90°C for 1.5 hrs. before adding sulfur. |
| 13 | air; 2% sulfur | 2 | 3.5 | — | 79 | |
| 14 | 1% tris (hydroxy methyl) nitromethane | 5 | 4 | — | 79 | — |
| 15 | 2% tris (hydroxy methyl) nitromethane | 5 | 3.5 | 4.5 | 77 | — |
| 16 | 4% p-nitrotoluene | 5 | 3.5 | 6.0 | 82 | — |
| 17 | 4% p-nitrotoluene | 0 | 4 | 5.5 | 86 | — |
| 18 | 1% tris (hydroxy methyl) nitromethane | 15 | 3 | — | 77 | — |
| 19 | 3% o+p-nitrotoluene | 5 | 5 | — | 81 | — |

[1]% by wt. of creosote.
[2]Reflux time of zero means creosote and neutral compound were heated to reflux and immediately distilled.
[3]Cleveland Electric Illuminating color code after 72 hours exposure to U.V. light and air at 80°C.
[4]5% pentachlorophenol in P-9 oil gave a CEI color of 3.5.
[5]Based on creosote charged, exclusive of neutral compound. Distilled to 300°C./60 mm.
[6]CEI on freshly distilled treated creosote.
[7]Treated creosote stored in air at 160°F. for 16 hours, then at 25°C. for 8 hours in the presence of a steel coupon repeated three times for a total of 72 hours.
[8]Refluxed for 5 minutes before distillation gave 18% residue.
[9]Refluxed for 30 minutes before distillation gave 18% residue.

TABLE II

Nitrobenzene was reacted with a Creosote A in a series of experiments shown in Table II to determine residence times and quantities necessary to obtain an improved creosote wood preservative with a light color. The Table shows the quantity of nitrobenzene used, the residence time of refluxing, the CEI color number before stabilization and after stabilization, and the weight percent of recovered distillate.

Table II
The Treatment of Creosote A with Nitrobenzene To Obtain an Improved Creosote Wood Preservative with a Light Color

| Run No. | Nitrobenzene[1] | Residence Time of Reflux[2] (min.) | CEI No.[3,4] Before[6] Stabilization | After[7] Stabilization | Wt.%[5] Recovered by Distillation |
|---|---|---|---|---|---|
| 23 | 6 | 70 | 4 | — | 70 |
| 24 | 10 | 7 | 3 | — | 90 |
| 25 | 3 | 5 | 4 | — | 76 |
| 26 | 4 | 15 | 4 | — | 80 |
| 27 | 5 | 30 | 3.5 | — | 77 |
| 28 | 4 | 0 | 3 | — | 83 |
| 29 | 3 | 0 | 4.5 | — | 83 |
| 30 | 2 | 0 | 4.5 | — | 83 |
| 31 | 1 | 0 | 4.5 | — | 83 |
| 32 | 1 | 1 | 3 | 6 | 79 |
| 33 | 2 | 2 | 4 | — | 81 |
| 34 | 2 | 1 | 4.5 | — | 81 |
| 35 | 3 | 1 | 4.0 | 5.0 | 81 |
| 36 | 1 | 2 | 4.5 | — | 81 |
| 37 | 3 | 2 | 4 | — | 84 |
| 38 | 1 | 3 | 4 | — | 81 |
| 39 | 2 | 3 | 4 | — | 81 |
| 40 | 3 | 3 | 4 | — | 81 |
| 41 | 1 | 4 | 3.5 | 5.0 | 81 |
| 42 | 2 | 4 | 4 | — | 84 |
| 43 | 3 | 4 | 3.5 | 5.0 | 84 |

Table II-continued

The Treatment of Creosote A with Nitrobenzene To Obtain an Improved Creosote Wood Preservative with a Light Color

| Run No. | Nitro-benzene[1] | Residence Time of Reflux[2] (min.) | CEI No.[3,4] Before[6] Stabilization | CEI No.[3,4] After[7] Stabilization | Wt.%[5] Recovered by Distillation |
|---|---|---|---|---|---|
| 44 | 3 | 15 | 4.5 | — | 80 |

[1] % by wt. of creosote.
[2] Reflux time of zero means creosote and nitrobenzene were heated to reflux and immediately distilled.
[3] Cleveland Electric Illuminating color code after 72 hours exposure to U. V. light and air at 80°C.
[4] 5% pentachlorophenol in P-9 oil gave a C.E.I. color of 3.5.
[5] Based on creosote charged, exclusive of reagent. Distilled to 300°C./60 mm.
[6] C.E.I. on freshly distilled treated creosote.
[7] Treated creosote stored in air at 160°F. for 16 hrs., then at 25°C. for 8 hrs. in the presence of a steel coupon repeated 3 times for a total of 72 hours.

According to the provisions of the patent statutes, the principal, preferred construction and mode of operation of the invention have been explained and what is considered to represent its best embodiment has been illustrated and described. However, it should be understood that within the scope of the appended claims the invention may be practiced otherwise than specifically illustrated and described.

We claim:

1. A method of preparing an improved creosote wood preservative having a lighter color and reduced tendency for formation of a crud deposit on treated wood from a coal tar creosote, comprising:
   a. refluxing the coal tar creosote with one or more of the neutral compounds selected from the group consisting of paraformaldehyde, nitrobenzene, nitrotoluene, tris (hydroxymethyl) nitromethane, aluminum, zinc and sulfur; and
   b. distilling the refluxed creosote to an end temperature in the range of 395°–410°C. at atmospheric pressure and to produce a distillate as the improved creosote wood preservative.

2. A method according to claim 1 wherein the distillation is at a temperature in the range of 285°–300°C at a reduced pressure.

3. A method according to claim 1 which includes cooling the refluxed creosote to a temperature in the range of 120°–175°C before the refluxed creosote is distilled.

4. A method according to claim 1 which includes dehydrating the coal tar creosote with heat to remove moisture from the coal tar creosote prior to refluxing in order to avoid dilution of the neutral compound.

5. An improved creosote wood preservative prepared according to the method defined in claim 1.

6. A method according to claim 1 which includes removing the compounds anthracene, phenanthrene and carbazole from the improved creosote wood preservative.

7. A method of preparing an improved creosote wood preservative having a lighter color and reduced tendency for formation of a crud deposit on treated wood from a coal tar creosote comprising:
   a. dehydrating a coal tar creosote with heat to remove the moisture from the coal tar creosote,
   b. collecting the low boiling compounds of the coal tar creosote that steam distill during dehydration,
   c. refluxing the dehydrated coal tar creosote with at least 5% paraformaldehyde for at least five minutes,
   d. cooling the refluxed creosote to a temperature in the range of 120°–175°C,
   e. distilling the cooled refluxed creosote to an end temperature in the range of 395°–410°C at atmospheric pressure to produce a distillate; and
   f. adding the collected low boiling compounds to the distillate to produce an improved creosote wood preservative.

8. An improved creosote wood preservative prepared according to the method defined in claim 7.

* * * * *

UNITED STATES PATENT OFFICE
CERTIFICATE OF CORRECTION

PATENT NO. : 3,973,971
DATED : August 10, 1976
INVENTOR(S) : Nicholas P. Greco et al It is certified that error appears in the above-identified patent and that said Letters Patent are hereby corrected as shown below:

Column 11, line 35, after 'trotoluene,' insert -- nitroxylene, --.

Signed and Sealed this

Fifteenth Day of February 1977

[SEAL]

Attest:

RUTH C. MASON
Attesting Officer

C. MARSHALL DANN
Commissioner of Patents and Trademarks